United States Patent [19]
Martin et al.

[11] Patent Number: 5,399,172
[45] Date of Patent: Mar. 21, 1995

[54] CATHETER HAVING GANGED ROTARY VALVES

[75] Inventors: Geoffrey S. Martin, Mississauga; Charles G. Shepherd, Oakville, both of Canada

[73] Assignee: Med-Pro Design, Inc., Mississauga, Canada

[21] Appl. No.: 264,279

[22] Filed: Jun. 23, 1994

[51] Int. Cl.⁶ .................................. A61M 5/00
[52] U.S. Cl. ........................... 604/248; 137/862
[58] Field of Search .............. 604/248, 29, 32, 43, 604/89, 93, 280–284; 137/862, 864, 887, 607; 251/231

[56] References Cited

U.S. PATENT DOCUMENTS

| | | | |
|---|---|---|---|
| 3,411,534 | 11/1968 | Rose | 137/595 |
| 4,512,372 | 4/1985 | Lew et al. | 137/862 |
| 4,595,005 | 6/1986 | Jinotti | 128/205.24 |
| 4,648,868 | 3/1987 | Hardwick | 604/32 |
| 5,084,031 | 1/1992 | Todd et al. | 604/248 |
| 5,324,274 | 6/1994 | Martin | 604/248 |
| 5,329,921 | 7/1994 | Soiaris et al. | 604/248 |

FOREIGN PATENT DOCUMENTS 545218 2/1932 Germany .................................. 30/5

Primary Examiner—C. Fred Rosenbaum
Assistant Examiner—Manuel Mendez
Attorney, Agent, or Firm—Rogers & Scott

[57] ABSTRACT

A catheter is provided having a main body defining two lumens and a connection structure at a proximal end of the main body. This structure includes a housing attached directly to the main body and defining a pair of passages connecting one to each of the lumens, and a pair of rotary valves operable to open and close the passages. The rotary valves are operable manually about individual axes by operators attached to the valves to turn the valves. The operators may be ganged for movement together to move both valves simultaneously between open and closed positions.

14 Claims, 2 Drawing Sheets

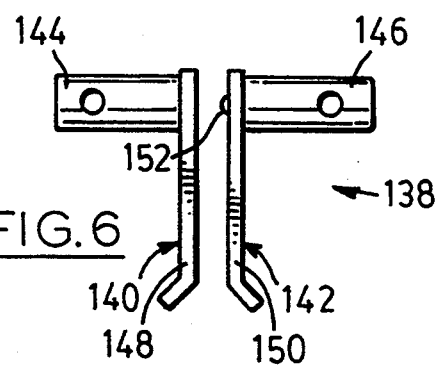
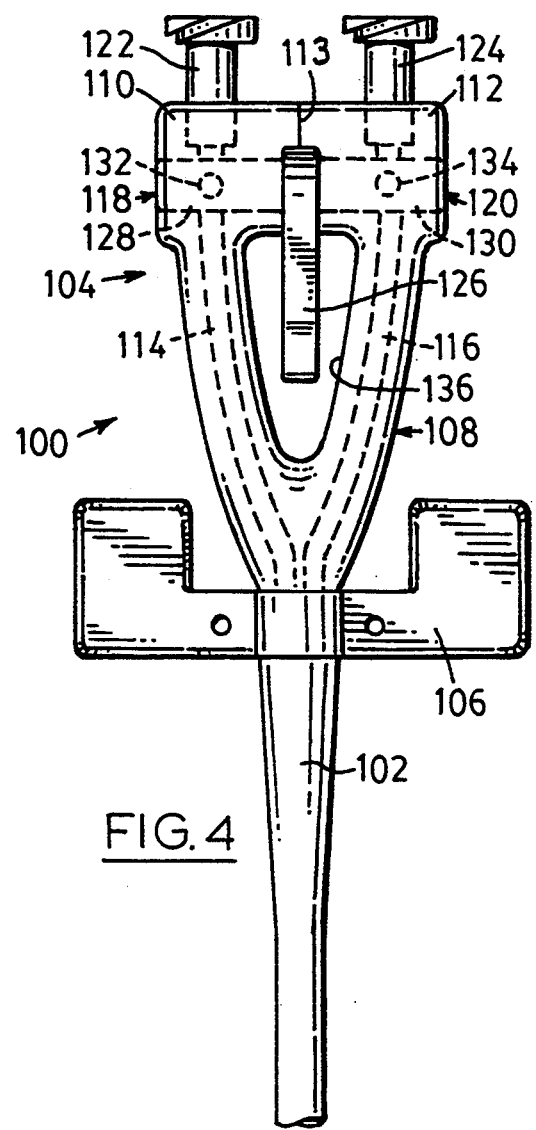
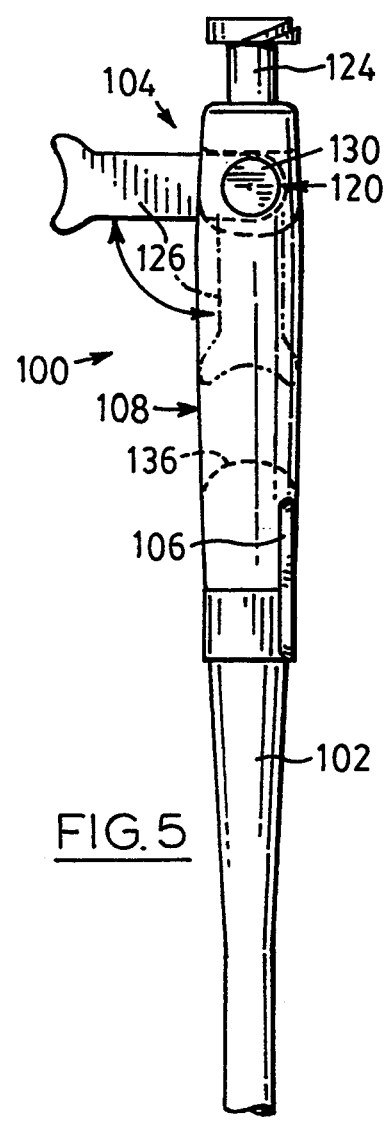

CATHETER HAVING GANGED ROTARY VALVES

BACKGROUND OF THE INVENTION

This application relates to catheters having two lumens and used in procedures requiring intrusion into the blood circulation system of a patient, and normally referred to as vascular access catheters. More particularly, the invention relates to such catheters having a connection structure at the proximal end including a pair of rotary valves operable to control flow through the lumens.

FIELD OF THE INVENTION

Vascular access catheters have been developed as single lumen, dual lumen or multi-lumen catheters and are used for a variety of procedures, all of which involve intrusion into the blood circulatory system. The main body of the catheter is designed for this intrusion and the proximal or outer end includes extensions, one for each lumen. It is common practice to make these extensions from flexible tubing with each of the tubes fitted with a luer lock connector at its free end for attachment to fluid lines, and also for closing and sealing the lumens when the catheter is not in use. Because these connectors may fail, it is also common practice to place a clamp about each of the extensions so that this can be used to close the extension if needed.

This second line of defence is made necessary because it is possible that the luer lock and its cap may fail due to misuse, or to simple flaws created during manufacture. It is evident that should the lines of defence fail while the catheter is in place, the patient is at risk of bleeding to death or suffering an air embolism if the failure is not detected very quickly.

Flexible tubes and clamps are not entirely satisfactory. The most serious problem is that the clamps close the tubes by a pinching action and if the clamp is in place for a significant length of time, it is not uncommon that the tubing will not recover when the clamp is released. The resulting crease in the tubing causes flow problems and in extreme cases the catheter has to be removed because the tube is no longer patent. The problem is most prevalent on catheters that have thermoplastic tubular extensions made from or polyurethane (PU). Also the problem is exacerbated by the fact that the extensions are attacked in a mild way by organic solvents such as alcohol that is always present in heparin, the anti-coagulant drug of choice used in catheters to maintain the patency of the catheter when not in use.

An alternative to PU is silicone rubber which is not attacked by solvents such as alcohol. Consequently the walls will not stick to one another, and this combined with the good rebound properties, make it suitable for use as extension tubes. Although some manufacturers use silicone rubber extensions for this reason, there is a secondary problem which has resulted in silicone rubber being superseded by PU. The problem relates to the fact that silicone is not thermoplastic and does not bond readily. Consequently if silicone rubber is to be used the tubes must be engaged using a friction fit alone and of course such a fit is subject to disconnection and adds another risk factor to the use of the catheter. It is therefore most common to use PU extensions which are permanently bonded to the remainder of the catheter.

There are other problems associated with the use of clamps. The structure needed for the clamps is bulky and unwieldy. It has also been found that unless the clamps are aligned accurately before they are engaged, they can be disengaged by a minor impact and such disengagement is visually evident only by close scrutiny.

Accordingly it is an object of the present invention to provide vascular access catheters having a structure for opening and closing the flow through the catheter which is reliable, maintains patency regardless of the time during which the catheter is not in use, and which is compact and convenient both to store when not in use and to operate in use. It is also an object of the invention to provide structure which provides a reliable visual indication of whether or not the structure is open or closed to flow.

SUMMARY OF THE INVENTION

A catheter is provided having a main body defining two lumens and a connection structure at a proximal end of the main body. This structure includes a housing attached directly to the main body and defining a pair of passages connecting one to each of the lumens, and a pair of rotary valves operable to open and close the passages. The rotary valves are operable manually about individual axes by operators attached to the valves to turn the valves. The operators may be ganged for movement together to move both valves simultaneously between open and closed positions.

BRIEF DESCRIPTION OF THE DRAWINGS

FIG. 4 is a front view of a second embodiment of catheter according to the invention with an operator in closed position;

FIG. 5 is a side view of the second embodiment with the operator shown in an open position, and also shown in ghost outline in the closed position; and FIG. 6 is an exploded view of a two-part operator which could be used in the second embodiment.

DESCRIPTION OF THE PREFERRED EMBODIMENTS

Figure 1:
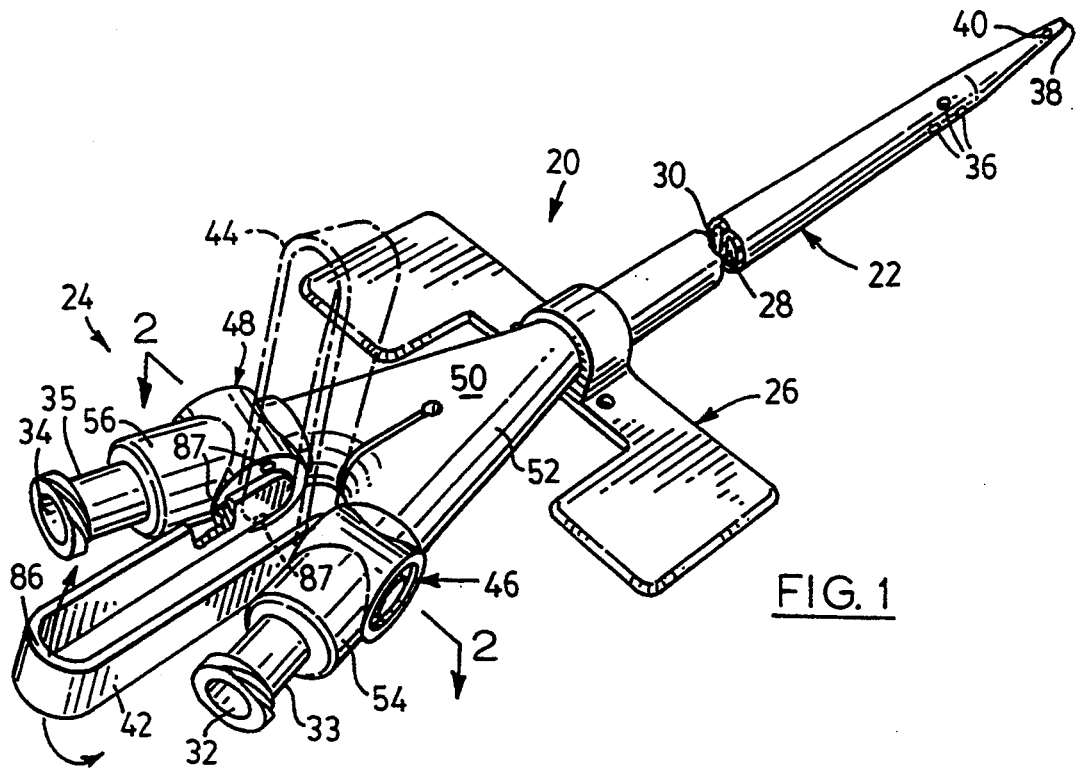
FIG. 1 is a diagrammatic perspective view of a preferred embodiment of a catheter according to the invention and enlarged to better show the parts, the view including an operator shown in a closed position in full outline and in an open position in ghost outline.

Reference is made firstly to FIG. 1 which illustrates (to an enlarged scale) a catheter designated generally by the numeral 20 and consisting essentially of three main parts, namely elongate main body 22, a connection structure designated generally by the numeral 24, and a suture wing structure 26 which is rotatably mounted on the catheter where the main body 22 meets the connection structure 24. The main body is exemplary of different cross sections and in this case includes a pair of side-by-side lumens 28, 30 which are connected to passages 32, 34 starting in luer connectors 33, 35 and continuing through structure 24 as will be described more fully with reference to FIG. 2. For the moment it is sufficient to understand that these passages provide two different functions in most uses. The passage 32 connects to the lumen 28 which is an intake lumen terminating at side openings 36, and the passage 34 connects to a return lumen 30 which extends to the tip of the catheter ending at an end opening 38 and side openings 40. As a result, when the catheter is attached to equipment such as a dialysis machine, blood would be withdrawn via passage 32 and after treatment, returned to passage 34 so that within the vascular access, blood would flow through side openings 36 into the catheter and returned through end opening 38 and side openings 40.

During treatment and between treatments, it is necessary to close off these flows and then to re-establish them. It is clearly necessary to provide a visual indication of the status of the catheter, both in the open and in the closed positions. This visual indication should be as evident as possible so that even cursory examination of the catheter would reveal the status of the catheter. To this end, the catheter shown in FIG. 1 includes an operator 42 moveable angularly between the position shown in full outline where the passages are closed, and an open position indicated in ghost outline at 44. The operator is coupled to respective first and second valves 46, 48. The valves are set in a housing 50 which includes a main portion 52 and from that depends a pair of divergent valve housings 54, 56 containing the valves 46, 48. It will now be evident that the operator 42 controls both valves simultaneously and is therefore "ganged".

Figure 2:
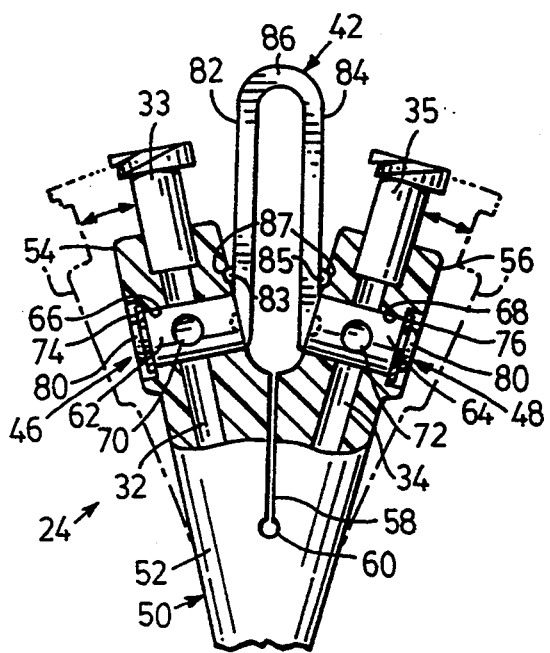
FIG. 2 is a sectional view of the catheter on line 2—2 of FIG. 1 and showing in ghost outline how a housing would be flexed during assembly.

Reference is next made to FIG. 2 to more fully describe the connection structure designated generally by the numeral 24.

As seen in FIG. 2, the main portion 52 of the housing 50 is generally V-shaped in that it widens as it extends away from a direct connection to the proximal end of the main body 22. However the housing is substantially of constant thickness so that it presents a flat appearance. Also, the result is that the transverse cross-section of the housing increases as it widens so that it has maximum flexibility near the main body for reasons which will be explained.

The housing 50 defines a narrow slot 58 which extends axially of the catheter from between the respective valve housings 54, 56, terminating at a stress relieving opening 60. This slot facilitates assembly as will be described.

The valves 46, 48 include respective barrels 62, 64 which are sliding fits within corresponding openings 66, 68 formed in the housing. The axes of these openings lie respectfully at right angles to the associated passages 32, 34 and the barrels 62, 64 are attached at their adjacent ends to the operator 42. The barrels also define respective through holes 70, 72 which, when aligned with the passages 32, 34 by moving the operator into the ghost outline position shown in FIG. 1, provides through flow along the passages 32, 34. Of course in the position shown in FIG. 2, the operator is in a position where the barrels have closed the passages.

Although the axes of the barrels lie in a common plane, they are angled relative to one another in order to put the barrels at right angles to the passages 32, 34. The amount of this misalignment is dependent upon the structure designed for the housing 50 and a different arrangement will be described with reference to FIG. 4. It will be appreciated that the material selected for the housing will be compatible with that of the main body as is common practice in the art. Also the grade of material will permit some flexing of the housing to facilitate assembly.

The respective barrels are located in the associated openings by end washers 74, 76 located in recesses in the valve housings and retained in position by respective enlargements 78, 80 on the ends of the barrels.

Figure 3:
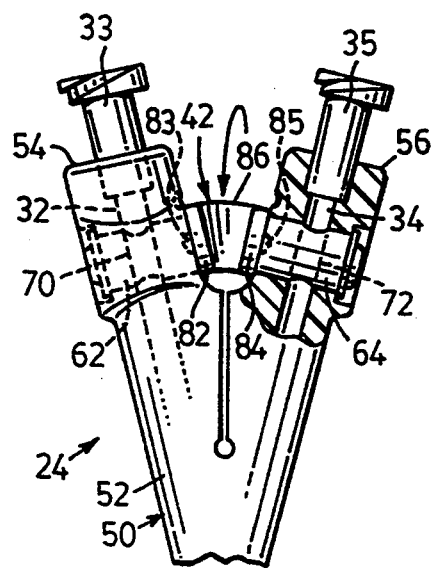
FIG. 3 is a view similar to FIG. 2 with the operator in the open position.

It should also be noted in FIGS. 1 and 2 that the operator 42 is essentially two arms 82, 84 extending in parallel from the associated barrels and joined at a bale 86 at the outer extremity of the operator. There is therefore an inherent flexibility in the operator which is needed to accommodate the misalignment of the barrels as the operator is moved between open and closed positions. Some of this flexibility is illustrated in FIG. 3 where the operator is in the open position and the through holes 70, 72 are in line with the associated passages 32, 34.

It will be evident from a review of FIGS. 1 and 2 that the connection structure 24 is both compact and convenient both for the patient and for an attendant operating the catheter. The housing is shaped to flex so that it is held down by a surgical dressing, the small misalignments between the housing and the main body will be accommodated. Further, there is a very clear indication when the catheter is open or closed because the operator 42 is of a significant dimension relative to the remainder of the catheter and the condition of the catheter will be evident from the observed position of the operator. As mentioned briefly previously the arrangement is such that the connection structure 24 is relatively flat when the operator is closed. In other words, the accommodation of the valves is done by providing width in the structure 24 as opposed to depth measured at right angles to the plane containing the axes of the barrels 62, 64 (FIG. 2). In this context, the term "flat" is intended to indicate that this front to back depth extending between major surfaces of the structure has been minimized in order to improve the convenience for the patient when the catheter is in place but not in use and not connected to dialysis or other equipment.

It is also to be noted that the catheter is reversible in the event that the catheter has to be rotated within the wing structure 26. The catheter can be turned and the operator 44 can be operated from the opposite side of that shown in FIG. 1. This is very important because the same visual indication is then apparent regardless of which is the front and which is the back of the catheter when viewed by an attendant. This is of particular value when using a catheter having lumens of the type shown in FIG. 1 where rotation is made necessary by the limitations of the side-by-side design. These limitations include the fact that the openings 36 must by design be on one side of the catheter and suction applied through the catheter can draw the side of the catheter into contact with a blood vessel. The remedy is then to rotate the catheter. This problem is less evident in coaxial catheters where the inlet openings are positioned about the entire periphery of the catheter. A main body of the coaxial type can of course be substituted for that shown in FIG. 1. The connections between the main body 22 and the connection structure 24 are well advanced in the art and therefore not described.

It will be clear from FIGS. 1 to 3 that when the operator 42 is moved between the open and closed positions, the misalignment of the axes of rotation of the valves 46, 48 will cause some change in shape of the operator as has been described with reference to FIG. 3. As a result the operator must be designed to flex readily so that minimal energy will be stored and the force to be applied to move the operator will also be minimized. To assist positive location, the arms 82, 84 have respective rounded projections 83, 85 (FIG. 2) which resiliently engage in corresponding depressions in the valve bodies. Exemplary depressions are seen at 87 in FIG. 1. Each projection can locate in a depression to locate the operator in the valve closed position, and two other depressions can be used for one of the two open positions as previously explained.

Although the catheter has been described with a single operator, it will be evident that with minor changes it will be possible to provide individual arms such as arms 82, 84 without the bale 86. It will still be convenient to operate both of the valves simultaneously by gripping both of the arms and moving them together but it is also possible to move the arms individually. The term "ganged" in the present context is intended to mean that the operator could be a single operator as shown in FIG. 2 or it could be two separate operators positioned to be operated simultaneously by simple movement of a finger or a thumb.

Reference is next made to FIG. 4 to show an alternative embodiment which is perhaps more desirable where more security for an operator is required. As seen in FIG. 4, a catheter designated generally by the numeral 100 has a main body 102 and a connection structure indicated generally by the numeral 104 attached directly to the main body. As usual, a wing structure 106 is included.

In the embodiments shown in FIGS. 4 and 5, a housing 108 is generally V-shaped terminating at respective valve housings 110, 112 which are attached to one another after assembly by adhesive at a joint 114. The structure 104 defines passages 114, 116 which pass through valves 118 and 120 respectively and which terminate at luer connectors 122, 124.

The catheter includes an operator 126 which is attached to aligned barrels 128, 30 passing through the respective valve housings 110, 112 and defining through holes 132, 134. As shown, the operator is in the closed position, when it is moved from the closed position shown in FIG. 4 to the an open position (FIG. 5) the through holes would be in alignment with the passages 114, 116.

The structure shown in FIGS. 4 and 5 would be assembled by first separating the valve housings 110, 112 using the flexibility of the V-shaped main portion of the housing 108. The deflection is sufficient to permit the operator 126 and associated barrels 128, 130 to be engaged with the valve housings and the valve housings are then brought together in alignment and the joint 114 is closed. The assembly would be completed by applying an adhesive or bonding agent to the joint before closing it. An alternative of course would be to make a mechanical connection.

Once assembled, the structure shown in FIGS. 4 and 5 has the advantages of being very compact, convenient to use, and it provides some protection for the operator 126 against accidental opening. Once the operator is in the position shown in FIG. 4, it is essentially confined within an elongate opening 136 and, as seen in FIG. 5, the extent of the operator is such that it is within the confines of the depth or thickness of the connection structure 104 when it is in the closed position. On the other hand, the extent of the operator 126 is such that when it is in the open position as shown in full outline in FIG. 5, there is a very ready visual indication of the status of the catheter.

The opening 136 also has another purpose. The transverse cross-section of the housing is minimized by the presence of the opening to enhance the flexibility near the junction with the main body.

As described previously with reference to FIGS. 1 to 3, the convenience for the user of a catheter of this type is due to the compactness and flatness of the connection structure. This is emphasized in the structure shown in FIGS. 4 and 5 due to the fact that the operator is contained within the connection structure as opposed to extending beyond it as seen in FIG. 1. Consequently the FIG. 4 structure may well be preferred in some circumstances.

Another advantage of the FIG. 4 structure is the fact that although the barrels 128, 130 of the valve lie in the same plane, they are also coaxial. This is an advantage in that the operator 126 can be a simple structure as opposed to the more complicated structure shown in FIG. 1. It will also be evident that it would be a simple matter to modify the operator 126 into two parts. As seen in FIG. 6, an operator 138 has first and second parts 140, 142 having respective barrels 144, 146 and arms 148, 150. The arm 150 carries a central small projection 152 located on the axis of rotation to separate the arms and minimize friction between them. Although the operator 138 is ganged to be operated by one finger, the individual pans 140, 142 allow the valves to be moved independently.

These and other structures are within the scope of the invention as claimed.

We claim:
1. A catheter comprising:
an elongate main body including a pair of lumens and extending between proximal and distal ends; and
connection structure including a housing attached directly to said proximal end and defining a pair of passages forming continuations of the respective lumens, a pair of rotary valves including valve housings formed in said housing and having respective axes of rotation lying in a common plane and including barrels rotatable in said valve housings on actuation of the valves, and a ganged operator attached to the barrels between the barrels for actuating the valves.

2. A catheter as claimed in claim 1 in which the operator has two separate parts having respective arms attached one to each of the barrels, and in which the arms are adjacent one another with both valves open or closed so that the arms can be moved in unison by engaging the arms simultaneously or independently as required.

3. A catheter as claimed in claim 1 in which said axes of rotation lie at right angles to the respective passages within the valves.

4. A catheter as claimed in claim 1 in which said axes of rotation are coaxial.

5. A catheter as claimed in claim 1 in which the housing defines a slot extending axially with respect to the main body of the catheter, the slot being between the valve housing to permit deflection of the housing outwardly during assembly to create space to enter the barrels.

6. A catheter as claimed in claim 1 in which the housing includes a joint used to attach the valve housings to one another after assembly.

7. A catheter as claimed in claim 1 in which the housing defines a through opening between said axes and the main body and between said passages, and in which the operator is located within said elongate opening when the valves are closed.

8. A catheter as claimed in claim 1 in which the operator is located when the valves are closed, essentially in said plane containing said axes and generally parallel to said passages.

9. A catheter as claimed in claim 1 in which the operator is located, when the valves are closed between said axes and the main body in a through opening defined in the housing.

10. A catheter as claimed in claim 1 in which the operator lies generally in said plane when the valves are closed and is moveable angularly away from the plane in either direction into one of two open positions in which the operator is essentially at right angles to said plane.

11. A catheter as claimed in claim 10 in which the operator has two separate portions attached one to each of the barrels and in which the arms are adjacent one another with both valves open or closed so that the arms can be moved in unison by engaging the arms simultaneously or independently as required.

12. A catheter as claimed in claim 10 in which said axes of rotation lie at right angles to the respective passages within the valves.

13. A catheter as claimed in claim 10 in which said axes of rotation are coaxial.

14. A catheter as claimed in claim 10 in which the housing defines a through opening between said axes and the main body and between said passages, and in which the operator is located within said elongate opening when the valves are closed.

* * * * *